(12) United States Patent
Kellnberger et al.

(10) Patent No.: US 12,369,971 B2
(45) Date of Patent: Jul. 29, 2025

(54) SYSTEMS AND METHODS FOR IMAGING IN CONNECTION WITH THERMAL ABLATION TREATMENTS

(71) Applicant: Varian Medical Systems, Inc., Palo Alto, CA (US)

(72) Inventors: Stephan Kellnberger, Erlangen (DE); Stanislav Tashenov, Heroldsbach (DE); Oliver Hornung, Unterleinleiter (DE)

(73) Assignee: Varian Medical Systems, Inc., Palo Alto, CA (US)

(*) Notice: Subject to any disclaimer, the term of this patent is extended or adjusted under 35 U.S.C. 154(b) by 41 days.

(21) Appl. No.: 17/812,958

(22) Filed: Jul. 15, 2022

(65) Prior Publication Data
US 2024/0016539 A1    Jan. 18, 2024

(51) Int. Cl.
| | | |
|---|---|---|
| *A61B 18/00* | (2006.01) | |
| *A61B 8/00* | (2006.01) | |
| *A61B 8/08* | (2006.01) | |
| *A61B 8/12* | (2006.01) | |
| *A61B 18/14* | (2006.01) | |
| *A61B 18/18* | (2006.01) | |
| *A61B 90/00* | (2016.01) | |

(52) U.S. Cl.
CPC ........ *A61B 18/1482* (2013.01); *A61B 8/12* (2013.01); *A61B 8/4477* (2013.01); *A61B 8/485* (2013.01); *A61B 8/5246* (2013.01); *A61B 18/1815* (2013.01); *A61B 2018/00577* (2013.01); *A61B 2018/00982* (2013.01); *A61B 2018/00994* (2013.01); *A61B 2090/3784* (2016.02)

(58) Field of Classification Search
CPC ..... A61B 18/1482; A61B 8/12; A61B 8/4477; A61B 8/485; A61B 8/5246; A61B 18/1815; A61B 2018/00577; A61B 2018/00982; A61B 2018/00994; A61B 2090/3784

See application file for complete search history.

(56) References Cited

U.S. PATENT DOCUMENTS

| | | | | |
|---|---|---|---|---|
| 6,375,635 | B1 * | 4/2002 | Moutafis | A61B 17/3203 |
| | | | | 604/35 |
| 9,060,670 | B1 * | 6/2015 | Boctor | A61B 8/085 |
| 11,209,259 | B1 * | 12/2021 | Ma | G01N 21/1702 |
| 2001/0051802 | A1 * | 12/2001 | Woloszko | A61B 18/1482 |
| | | | | 604/35 |

(Continued)

FOREIGN PATENT DOCUMENTS

WO    2024015505 A1    1/2024

OTHER PUBLICATIONS

E. J. Alles et al., "Real-Time, Video-Rate and Depth-Resolved Imaging of Radio-Frequency Ablation Using All-Optical Ultrasound," 2018 IEEE International Ultrasonics Symposium (IUS), Kobe, Japan, pp. 1-9, doi: 10.1109/ULTSYM.2018.8580211. (Year: 2018).*

(Continued)

*Primary Examiner* — Amal Aly Farag
(74) *Attorney, Agent, or Firm* — Duane Morris LLP

(57) ABSTRACT

An ablation device includes a shaft and a radiofrequency (RF) emitter positioned in the shaft that delivers radiofrequency (RF) energy to create an ablation volume. The ablation device also includes an imaging sensor positioned in the tubular shaft configured to obtain imaging data of the ablation volume.

13 Claims, 9 Drawing Sheets

(56) References Cited

U.S. PATENT DOCUMENTS

| | | | |
|---|---|---|---|
| 2006/0178665 A1* | 8/2006 | Sloan | A61B 18/1477 606/41 |
| 2009/0221999 A1* | 9/2009 | Shahidi | A61B 34/10 128/898 |
| 2010/0168569 A1 | 7/2010 | Sliwa et al. | |
| 2012/0165667 A1 | 6/2012 | Altmann et al. | |
| 2013/0197363 A1 | 8/2013 | Rankin et al. | |
| 2014/0276052 A1* | 9/2014 | Rankin | A61B 18/1492 600/439 |
| 2015/0257779 A1 | 9/2015 | Sinelnikov et al. | |
| 2016/0374710 A1* | 12/2016 | Sinelnikov | A61B 17/3207 600/439 |
| 2017/0007324 A1* | 1/2017 | Kadamus | A61B 5/6847 |
| 2017/0224402 A1* | 8/2017 | Borsic | A61B 90/37 |
| 2020/0383661 A1 | 12/2020 | Gijsbers et al. | |
| 2021/0128106 A1* | 5/2021 | Salehi | A61B 8/4245 |
| 2021/0267680 A1* | 9/2021 | Sela | A61B 8/12 |
| 2022/0175405 A1 | 6/2022 | Deckman et al. | |
| 2022/0226046 A1* | 7/2022 | Mariappan | A61B 18/1492 |

OTHER PUBLICATIONS

International Search Report and Written Opinion for PCT/US2023/027614 issued Oct. 26, 2023.

\* cited by examiner

SYSTEMS AND METHODS FOR IMAGING IN CONNECTION WITH THERMAL ABLATION TREATMENTS

TECHNICAL FIELD

The present disclosure relates to systems and methods for imaging in connection with thermal ablation treatments. More specifically, the present disclosure relates to systems and methods that may use ablation probes that perform both ablation and imaging functions.

BACKGROUND

Ablation is a type of procedure that uses extreme temperatures (thermal) or microwave and electrical currents to destroy (ablate) cancer cells and tumors. In some circumstances such as when a patient is not suited for tumor removal, thermal ablation can be considered an alternative method of treatment. Thermal ablation of cancerous tissue with Radiofrequency (RF) or Microwave (MW) energy is frequently used for liver tumor treatment and is emerging as a true alternative to resection of liver tumors.

RF and MW ablation is often performed using one or more special needles or probes. The probe is inserted near to or into the target tissue, such as cancerous tissue, and electrical current sent through the probe heats the target tissue to high temperatures which destroys the target tissue. It is intended that the treatment produces a limited or targeted heating zone so that the treatment does not generally affect surrounding healthy tissue and limits or minimizes harm to the healthy tissue.

Ablation is typically preceded by a planning stage where a medical professional such as an interventional radiologist predetermines optimal probe paths for the procedure. Treatment involves placing an ablation probe into the target tissue or tumor using computed tomography (CT) image guidance or other probe tracking and guidance technologies such as stereotactic cameras. In general, planning and guidance can be performed by the medical professional.

Existing or traditional systems and methods suffer from various drawbacks. For example, once the medical professional initiates ablating the target tissue or tumor, there is no or limited real-time feedback on the actual volume of tissue that is being ablated. Anatomical factors affect the ablation volume and there are no simultaneous imaging techniques that provide full situational awareness during treatment. For example, blood flow in the nearby vessels cools the surrounding tissue and inhibits heating by the thermal ablation. Such factors lead to uncertainty of the actual ablation volume and exactly which tissue has been treated. As a result, a reliable determination of the ablating volume of the tumor cannot be confirmed during the procedure. Typically, the first possibility to verify the ablation volume is provided by an imaging scan that is done after the ablation procedure, where the medical professional confirms the tumor status. Subsequent treatments may be needed to re-ablate specific zones of the target tissue or tumor.

Additionally, RF and MW ablation generates microbubbles in the ablation area due to the interaction of high-frequency currents with soft tissue. The microbubbles interfere with imaging. These microbubbles represent a hyperechoic region or cloud (an area reflecting many sound waves) with strong contrast in an ultrasound image. The hyperechoic bubbles impact ultrasound imaging beyond the microbubble cloud, resulting in a partial representation of the ablation volume when using existing devices such as handheld ultrasound probes. There exists a need, therefore, for improved systems and method of performing ablation treatments that may allow for more information to be collected during the treatment such as imaging information that describes progress of the ablation treatment.

SUMMARY OF THE DISCLOSURE

In various embodiments of the present disclosure, systems and methods are provided that can obtain imaging information that describe the progress of an ablation treatment during the procedure. This information is an improvement over existing and traditional methods of treatment by providing real-time feedback regarding the ablation of a target tissue during treatment. This information can improve the effectiveness of the treatment and can reduce the likelihood that subsequent treatments are performed. The systems and methods of the present disclosure allow a medical professional to determine whether all or a desired portion of the target tissue has been destroyed during treatment. Furthermore, the systems and methods of the present disclosure can reduce and/or limit harm to healthy tissues that may be located close to the target tissue.

In some embodiments of the present disclosure, systems and methods are provide that can achieve up to full imaging coverage (360°) of the ablation volume by placing multiple transducers around the ablation volume. In some examples, ultrasound imaging may be integrated into ablation probes. In various examples, the ablation probes may facilitate up to full coverage of the ablation volume that is not possible with existing handheld or external imaging probes.

In addition, embodiments of the present disclosure can provide a miniaturized design based on fiber optics, eliminate interference between ultrasound and radiofrequency/microwave (RF/MW) signals (decoupling the imaging from the therapy), facilitate optical tracking of the ablation probe using computed tomography (CT) registration, and map an imaging overlay showing shear wave elastography (SWE) and a bubble cloud in one image for better tissue ablation evaluation.

In some embodiments, an ablation device may include a shaft and a radiofrequency (RF) emitter positioned in the shaft that delivers radiofrequency (RF) energy to create an ablation volume. The ablation device may also include an imaging sensor positioned in the tubular shaft configured to obtain imaging data of the ablation volume.

In one aspect, the shaft may include a distal end that is positioned at or near a target tissue during an ablation procedure and the RF emitter may be positioned closer to the distal end than the imaging sensor.

In another aspect, the RF emitter includes a microwave (MW) antenna.

In another aspect, the RF emitter includes a radiofrequency (RF) electrode.

In another aspect, the imaging sensor includes an ultrasound transducer.

In another aspect, the imaging sensor includes an all-optical ultrasound transducer.

In another aspect, the imaging device may be configured to operate simultaneously with the RF emitter during an ablation procedure.

In another aspect, the imaging sensor is a first imaging sensor and the ablation device further includes a second imaging sensor positioned in the shaft.

In another aspect, the RF emitter may be positioned between the first imaging sensor and the second imaging sensor.

In another aspect, the imaging device may be configured to operate in an imaging mode to collect imaging data and in a shear wave elastography (SWE) mode to collect elastography data from the ablation volume.

In some embodiments an ablation system is provided. The ablation system may include a probe configured to deliver RF energy to a target tissue in a patient and a first imaging sensor positioned to obtain first imaging data from a first direction relative to the target tissue. The ablation system may also include a second imaging sensor positioned to obtain second imaging data from a second direction relative to the target tissue. The first direction and the second direction are different and the second imaging sensor may be located internally of the patient.

In one aspect, the second imaging sensor may be located in the probe.

In another aspect, the second imaging sensor is configured to operate simultaneously with operation of the probe.

In another aspect, the first imaging sensor and the second imaging sensor may be both located in the probe.

In another aspect, the second imaging sensor may be located in the probe and may include an all-optical ultrasound transducer.

In another aspect, the second imaging sensor may include a silicon photonics based ultrasound transducer.

In some embodiments, a method of performing a radiofrequency (RF) therapy is provided. The method may include energizing an RF emitter located at or near a target tissue in a patient and obtaining first imaging data from a first direction relative to the target tissue. The method may also include obtaining second imaging data from a second direction relative to the target tissue and combining the first imaging data and the second imaging data to create an image of an ablation volume.

In one aspect, the second direction may correspond to a direction from inside the patient.

In another aspect, the step of energizing the RF emitter and at least one of obtaining the first imaging data and obtaining the second imaging data are performed simultaneously.

In another aspect, the first direction and the second direction may correspond to opposing sides of the target tissue.

In another aspect, the second imaging data may be obtained from an all-optical ultrasound transducer.

The above and other features, elements, characteristics, steps, and advantages of the present invention will become more apparent from the following detailed description of preferred embodiments of the present invention with reference to the attached drawings.

BRIEF DESCRIPTION OF THE DRAWINGS

The features and advantages of the present disclosures will be more fully disclosed in, or rendered apparent by the following detailed descriptions of example embodiments. The detailed descriptions of the example embodiments are to be considered together with the accompanying drawings wherein like numbers refer to like parts and further wherein.

DETAILED DESCRIPTION

Figure 1:
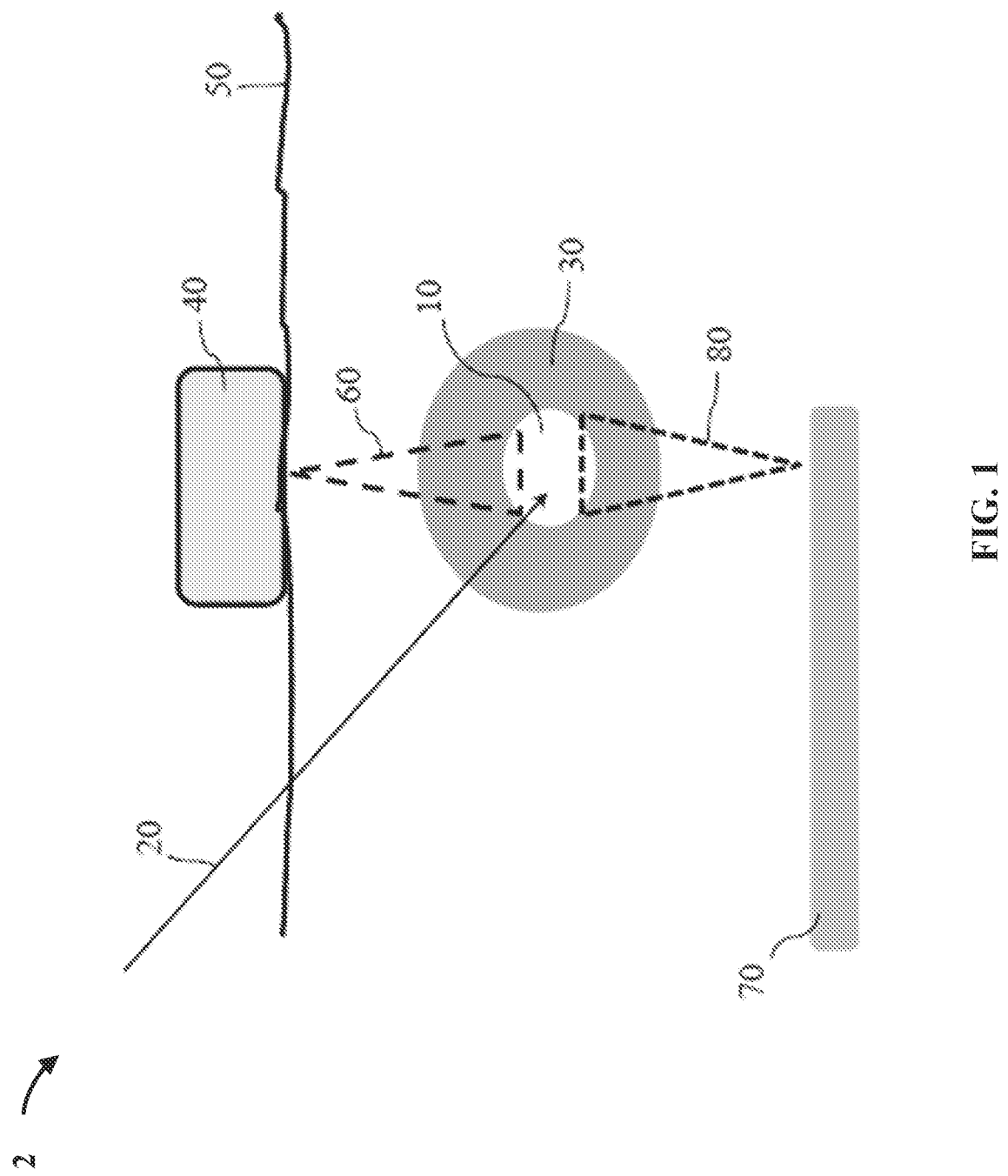
FIG. 1 is a diagram showing an ablation system in accordance with one embodiment of the present disclosure.

The description of the preferred embodiments is intended to be read in connection with the accompanying drawings, which are to be considered part of the entire written description of these disclosures. While the present disclosure is susceptible to various modifications and alternative forms, specific embodiments are shown by way of example in the drawings and will be described in detail herein. The objectives and advantages of the claimed subject matter will become more apparent from the following detailed description of these exemplary embodiments in connection with the accompanying drawings.

It should be understood, however, that the present disclosure is not intended to be limited to the particular forms disclosed. Rather, the present disclosure covers all modifications, equivalents, and alternatives that fall within the spirit and scope of these exemplary embodiments. The terms "couple," "coupled," "operatively coupled," "operatively connected," and the like should be broadly understood to refer to connecting devices or components together either mechanically, electrically, wired, wirelessly, or otherwise, such that the connection allows the pertinent devices or components to operate (e.g., communicate) with each other as intended by virtue of that relationship.

In the present disclosure the singular forms "a," "an," and "the" include the plural reference, and reference to a particular numerical value includes at least that particular value, unless the context clearly indicates otherwise. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

The present disclosure relates to systems and methods to improve or increase imaging of target tissue during an ablation procedure. Referring now to FIG. 1, an example ablation system 2 is shown. The ablation system 2 may include an ablation probe 20, a first imaging sensor 40, and a second imaging sensor 70. The ablation system 2 may be used, for example, during an ablation treatment in which a target tissue 10 is desired to be destroyed. The target tissue 10 may be a tumor, lesion, cancer, or other abnormal tissue in a patient. During the treatment, the ablation probe 20 may be inserted through the skin 50 of the patient with a distal end of the probe 20 positioned at or near the target tissue 10. The probe 20 may be any suitable ablation probe such as a radiofrequency (RF) ablation probe or microwave (MW) ablation probe that can cause the region at or near the distal end of the probe 20 to be heated to an elevated temperature that destroys tissue. The elevated temperature of the ablation zone may cause a bubble cloud 30 to be produced. It is desirable to obtain an image or other information regarding a position of the probe 20, a position and/or size of the bubble cloud 30, and/or a position of the heated ablation zone so as to determine whether the target tissue and the ablation zone overlap so that the target tissue is destroyed during the treatment.

The first imaging sensor 40 and the second imaging sensor 70 may be used during a treatment to obtain imaging data that can be used to generate images of target tissue 10, the probe 20, and/or the bubble cloud 30. The first imaging sensor 40 and the second imaging sensor 70 may be various suitable sensors, transducers or the like. The first imaging sensor 40 and the second imaging sensor 70 may be ultrasound transducers, for example. In various examples, the first imaging sensor 40 and the second imaging sensor 70 may be an electronic ultrasound transducer, an all-optical ultrasound transducer, a piezoelectric transducers (PZT), capacitive micro-machined ultrasonic transducer (CMUT), a silicon photonics based ultrasound transducer, or a piezoelectric polyvinylidene fluoride (PVDF) based transducer. In other examples, other imaging sensors can be used.

In the example shown, the first imaging sensor 40 and the second imaging sensor are positioned on opposing sides of the target tissue 10. This arrangement allows for a more complete image of the target tissue 10, the probe 20, and the bubble cloud 30 to be obtained and to provide information regarding their relative positions. The second imaging sensor 70 may use endoluminal ultrasound sensing during the ablation treatment. Endoluminal ultrasound sensing involves insertion of an ultrasound transducer or sensor inside a tube, duct, or hollow portion in the body of a patient such as a blood vessel, the stomach, or the intestines. The inserted ultrasound transducer is used to generate imaging data from inside the body. In one example, the system 2 may use one endoluminal ultrasound sensor. In other examples (not shown), the system 2 may include multiple endoluminal ultrasound sensors.

In the example shown, the first sensor 40 may be positioned on an exterior surface of a patient's skin 50 with a first imaging field 60 (represented by the dashed line triangle) directed toward the target tissue 10. The first imaging sensor 40 can be handheld or any other suitable transducer as previously described. The second imaging sensor 70 can be located at a different position than the first imaging sensor 40 and may preferably be positioned on a side of the target tissue 10 opposite to the first imaging sensor 40. The second imaging sensor 70 may be a second ultrasound transducer (e.g. intravascular or endoscopic) and can be an endoluminal ultrasound transducer and located to image the 'back-side' of the target tissue 10 (the 'back side' being an opposite side of the target tissue 10 from the first ultrasound transducer direction). The combination of the first imaging sensor 40 and the second imaging sensor 70 may capture up to and including a full 360° view of the ablation volume. The second imaging sensor 70 may have a second imaging field 80 (represented by the dotted line triangle). The second imaging sensor in combination with first imaging sensor 40 provides improved coverage of the bubble cloud and a more accurate representation of the tissue damaged during ablation compared to a conventional procedure using only a single imaging sensor.

In other embodiments (not shown), the system 2 may include variations to the structure and configuration shown in FIG. 1. For example, the system 2 may include more than two imaging sensors. The system 2 may include more than one endoluminal ultrasound sensor or other imaging sensor positioned inside a patient. The system 2 may also include more than one imaging sensor positioned on the skin 50 of the patient or otherwise located external to the body of the patient.

Figure 2:
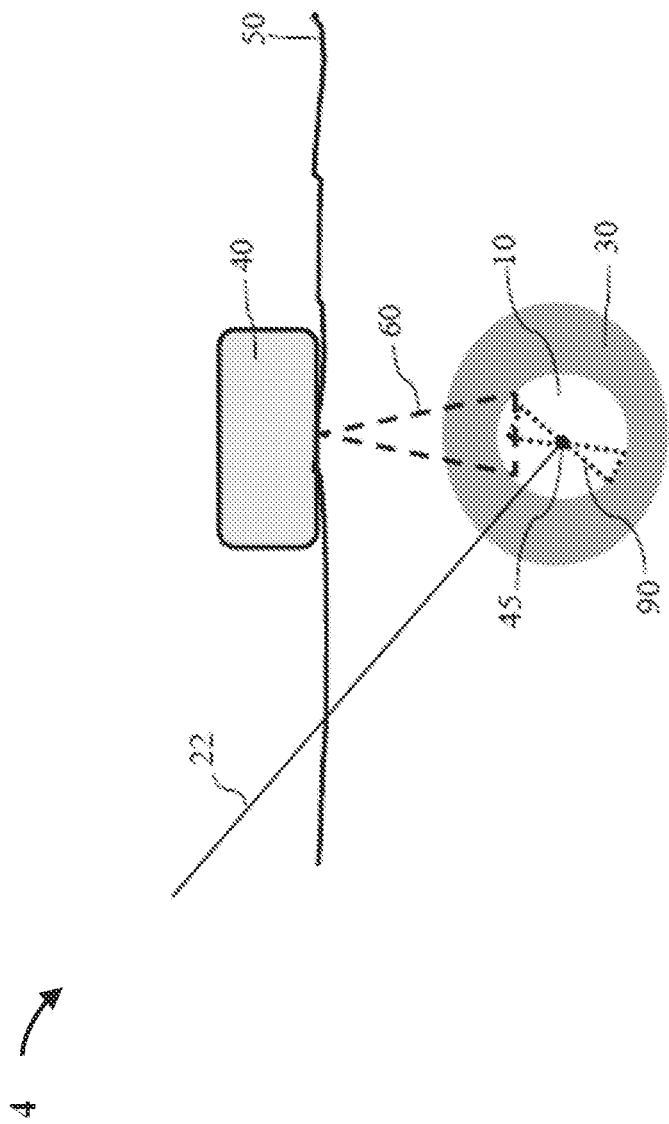
FIG. 2 is a diagram showing another ablation system that includes a hybrid RF/MW probe in accordance with another embodiment of the present disclosure.

Referring now to FIG. 2, another ablation system 4 is shown. In this example, the ablation system may include a first imaging sensor 40 and a hybrid probe 22. The first imaging sensor 40 may be similar to the first imaging sensor 40 described with respect to the ablation system 2 described above. The hybrid probe 22 may allow for multiple functions to be performed during an ablation treatment such as both ablation and imaging. For example, the hybrid probe 22 can include a radiofrequency (RF) emitter such as one or more RF electrodes and/or a microwave (MW) antenna. The hybrid probe 22 may also include an imaging sensor 45 such as an ultrasound transducer. Various ultrasound transducers may be used such as those ultrasound transducers described above regarding the second imaging sensor 70.

As shown in FIG. 2, the hybrid probe 22 may be positioned at or near a target tissue in a patient. The hybrid probe 22 may create a bubble cloud 30 around the target tissue 10. when the RF emitter is energized. Imaging data may be collected by the first imaging sensor 40 and the second imaging sensor 45. The first imaging sensor 40 may be located on a patient's skin 50 and collect imaging data using a first ultrasound field 60 (represented by the dashed line triangle) directed toward the target tissue 10. In this embodiment, the hybrid probe 22 can include the second imaging sensor 45 at or near the distal end of the probe 22 that provides ultrasound detection from a second ultrasound field 90 of the ablation volume from the distal end of the probe 22. The distal end being an end of a probe 22 that can be inserted into a patient and that is farthest from an end of the probe connectable to energy generation and sensing electronics. The second imaging sensor 45 can be positioned at any suitable location on the probe 22.

Data combined from both the first imaging sensor 40 and the second imaging sensor provides greater imaging coverage of the bubble cloud 30 and a more accurate representation of the target tissue 10 and/or the ablation volume as compared to a conventional procedure using only a single imaging device such as first imaging sensor 40. The second imaging sensor 45 may be rotated to obtain imaging data from a multiple directions from the distal end of the probe 22. The second imaging device 45 may be rotated within the needle 22 around its axis. In other examples, the second imaging device 45 may be configured as a phased array of imaging sensors positioned in the probe 22. The rotation of the second imaging 45 and/or a probe 22 that includes an array (or multiple arrays) of imaging sensors can permit up to full coverage (e.g., 360°) of the ablation volume from the isocenter of the ablation volume and/or a center of the target tissue 10.

In example probes 22 that include rotational imaging devices, the second imaging device 45 can be mounted and/or otherwise positioned at the distal end of the probe 22 and connected to a drive motor at the proximal end of the probe 22. The drive motor can rotate the second imaging device within the probe 22 to obtain a 360° image. In other examples that include a phased array, the second imaging device 45 may include multiple transducers positioned around a periphery or circumference of the second imaging device 45 in the probe 22. In some examples, 36 individual transducers can be positioned around the circumference of the second imaging device 45. In other examples, other numbers of transducers may be used. Such transducers may be triggered individually to acquire a 360° image. The various examples may present different advantages. Phased array imaging devices may have less motion artifacts due to the fact that they are not moved during imaging and potentially can provide faster imaging than rotational devices. Rotational devices, in comparison, may have higher resolution, but may also include non-uniform rotational distortion artifacts.

The ablation system 4 may provide both ablation and imaging functionality. In some examples, it is not desirable to perform imaging and ablation simultaneously as the RF/MW radiation can interfere with nearby imaging sensors. In such a case, ablation and imaging can be alternated, as further discussed below. In other examples, such as when the first or second imaging sensors are configured as all-optical ultrasound sensors, the imaging and ablation functions can be performed simultaneously in light of the lack of interference between the RF/MW energy and the all-optical ultrasound sensor operation.

During use of the ablation system 4, the second imaging sensor 45 can be located in the center of the ablation area or in its immediate vicinity. This arrangement provides various improvements over other arrangements in which the imaging sensor is positioned adjacent to or spaced apart from the ablation area and/or the target tissue 10. The positioning of the second imaging sensor 45 at a center of the ablation area (allowed by its location in the probe 22) provides a reduced distance between the imaging sensor and the bubble cloud 30 than other arrangements. In addition, the positioning of the second imaging sensor 45 at the center of the ablation area also results in improved imaging contrast over other arrangements. Still further, the positioning of the second imaging sensor 45 at the center of the ablation area provides improved imaging disturbance by the tissue surrounding the ablating area. The imaging data that is obtained is further improved over other arrangements because the ultrasound is minimally affected by surrounding structures such as bones, dense tissue, and air, which normally obscure ultrasound imaging when other arrangements are used.

In some embodiments, the second imaging sensor 45 can be rigidly fixed to the probe 22. With this integration, the second imaging sensor 45 and the RF emitter in the probe 22 are automatically physically registered with respect to each other, allowing direct overlap of the ablation volume on the imaged ablation volume with minimal mismatch. The integration of the second imaging sensor 45 and the RF emitted in the probe 22 does not require the second imaging sensor 45 to be separately positioned relative the ablation volume. Because the ultrasound sensor 45 is simultaneously and automatically located in the immediate vicinity or center of the ablation volume when the probe 22 is positioned at the target tissue 10, no special requirements to the power and sensitivity of the second imaging sensor 45 are needed. The power, sensitivity, and/or other operating parameters of the second imaging sensor 45 can be predetermined and easily configured. Accordingly, the ablation system 4 and the hybrid probe 22 provide various improvements over existing systems and devices. The hybrid probe 22, for example, can allow for a simultaneous sensing/imaging and ablation. The integration of the imaging function into the probe 22 also allows for a cost-efficient implementation, and reduces the complexity of the ablation treatment. Still further, the ablation treatment can be performed more effectively because of the improved imaging data that can be collected. This can improve the likelihood that the target tissue 10 is ablated during a single treatment and harm to surrounding and/or healthy tissues is minimized or reduced.

Figure 3:
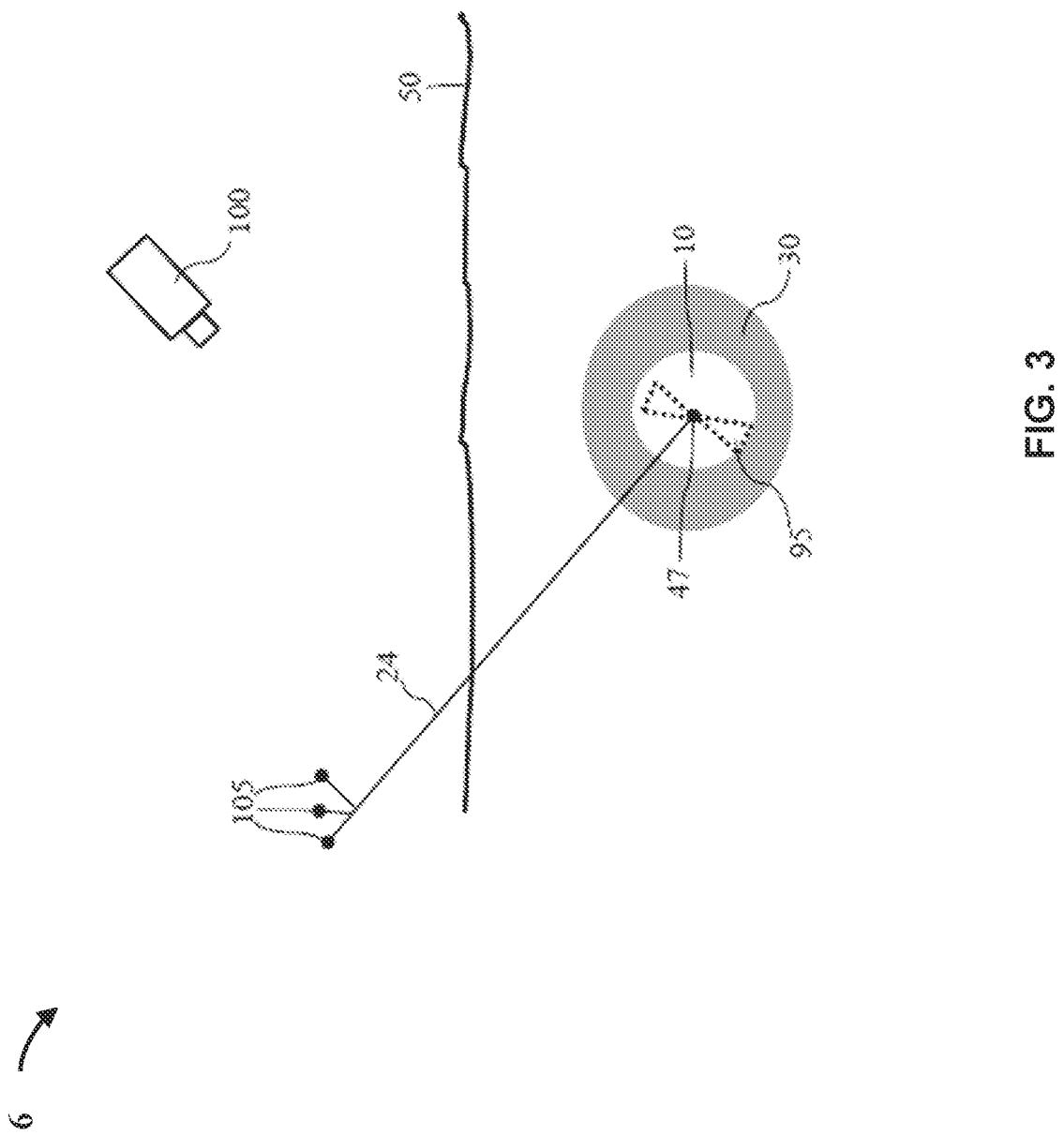
FIG. 3 is a diagram showing another ablation system that includes another hybrid RF/MW probe in accordance with another embodiment of the present disclosure.

Referring now to FIG. 3, another example ablation system 6 is shown. In this example, the ablation system 6 may include a probe 24 and a stereotactic imaging device 100. The probe 24, in this example, may include an imaging sensor 47 positioned at or near the distal end of the probe 24. The probe 24 may be similar to the probe 22 previously described and include both an RF/MW emitter and an imaging sensor to provide both ablation and imaging functionality. The imaging sensor 47, in this example, may be configured as an all-optical ultrasound transducer that allows simultaneous ablation and ultrasound imaging. All-optical transducers use pulsed or modulated light to generate ultrasound via the photoacoustic effect and can be less sensitive to electromagnetic noise than non-optical transducers that convert electrical energy to ultrasonic energy.

During use of the ablation system 6, the RF emitter at the distal end of the probe 24 may be positioned at a target tissue 10. The RF emitter may be energized to produce an ablation volume and may create a bubble cloud 30 around the target tissue 10. As shown, the probe 24 may also include markers 105 located on a portion of the probe 24. The markers 105 can be positioned on at a predetermined location on the probe 24. The stereotactic imaging device 100 can be used to obtain imaging data that detects a location of the markers 105. This imaging data can be used in combination with imaging data collected in advance of the ablation procedure to determine a location of the probe 24 relative to the target tissue 10. Optical tracking with the stereotactic imaging device 100 and the markers 105 of the probe 24 facilitates registration to preoperative CT images via imaging. In this example ablation system 6, an ablation procedure may no longer require an additional ultrasound transducer or other imaging sensor (i.e., on the patient's skin 50 or internal to the patient), as previously described. The stereotactic imaging device 100 can be various suitable imaging devices that allows for the directing of the distal end of the probe 24 in three planes using coordinates provided by medical imaging in order to reach the target tissue 10 in the patient's body.

In other examples and embodiments, the position of the probe 24 can be determined and/or tracked using other tracking and imaging. For example, electromagentic tracking may be used to determine the location of the probe 24. In still other examples, other marking and/or imaging methods can be used to determine a position of the probe 24.

In the embodiment shown, the imaging sensor 47 of the probe 24 can be an internal all-optical ultrasound transceiver at the distal end that allows ultrasound detection from an ultrasound field 95 of the ablation volume from the distal end of the probe 24. The probe 24 facilitates a fully integrated imaging and therapy solution in one device. The imaging sensor 47 may be rotated within the probe 24 in some examples. In other examples, the imaging sensor 47 can be configured as an array of imaging sensors. The rotation of the imaging sensor 47 and/or an array of imaging sensors can permit up to full coverage of the ablation volume from the isocenter of the ablation area. Full 360° views from the imaging sensor 47 can be obtained. With this arrangement, it is possible that imaging and therapy can be conducted simultaneously with one device and no additional ultrasound transducer(s) is required. In other examples, additional imaging sensors similar to the imaging sensor 47 can be added or used in addition to the imaging sensor 47. Such additional imaging sensors and transducers can also be tracked using the imaging device 100 and can provide further information and images of the target tissue 10, bubble cloud 30, surrounding tissues, and other bodily structures.

The ablation system 6 may provide for simultaneous therapy and imaging. The all-optical ultrasound transducer can allow the RF emitter and the imaging sensor to be operated simultaneously. Conventional piezoelectric transducers (PZT), capacitive micro-machined ultrasonic transducers (CMUT), and piezoelectric polyvinylidene fluoride (PVDF) based sensors cannot provide data to visualize the ablation area during the therapy mode due to electromagnetic interferences. The integration of the imaging sensor 47 as an all-optical ultrasound transducer and/or as a silicon photonics based ultrasound transducer in the probe 24 provides improved visualization of the ablation area over traditional or conventional treatments. The all-optical ultrasound transducers and/or the silicon photonics based ultrasound transducers can allow electromagnetic interference free detection of ultrasound during an ablation treatment.

The ablation systems and probes of the present disclosure provide other advantages over traditional systems and devices. In some examples, the probes of the present disclosure can provide sharp 360° boundary imaging of the bubble cloud registered to shear wave elastography (SWE) imaging which provides further information on tissue viability. The improved imaging of the bubble cloud that is allowed by the probes of the present disclosure can be used and combined with elastography imaging. The bubble cloud represents a hyperechoic volume and yields excellent contrast to surrounding tissues. The images of the bubble cloud provided by the probes of the present disclosure can yield excellent contrast to soft liver tissue with sharp boundaries, for example. As will be further described below, the ablation systems of the present disclosure can be used in various modes including a shear wave elastography (SWE) mode to provide information regarding necrosis or other characteristics of the target tissue.

Figure 4:
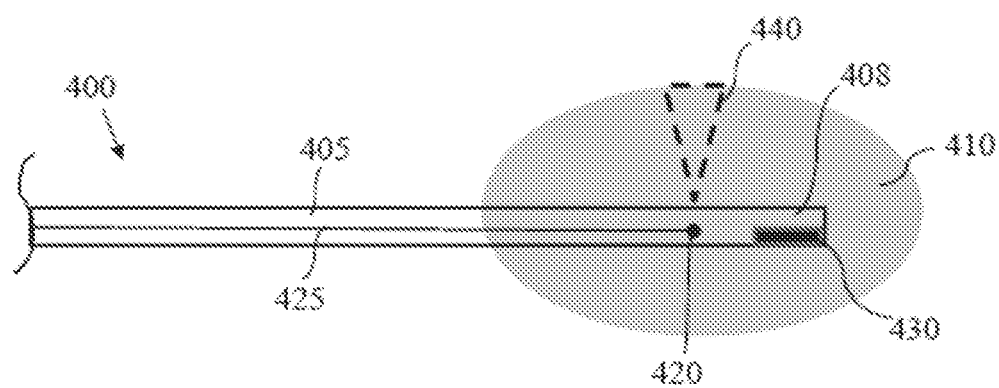
FIG. 4 is a side view of an example ablation probe that may be used on one or more ablation systems of the present disclosure.
Figure 5:
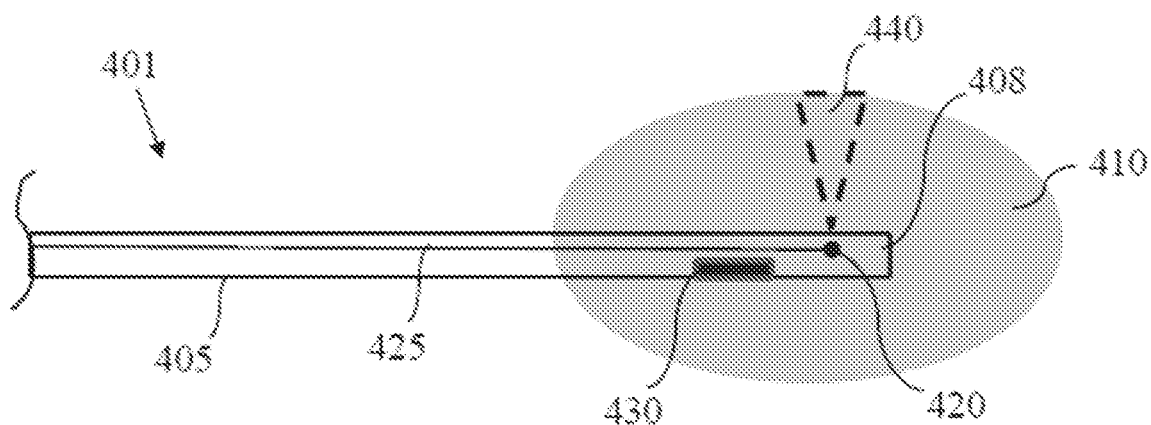
FIG. 5 is a side view of another example ablation probe that may be used on one or more ablation systems of the present disclosure.
Figure 6:
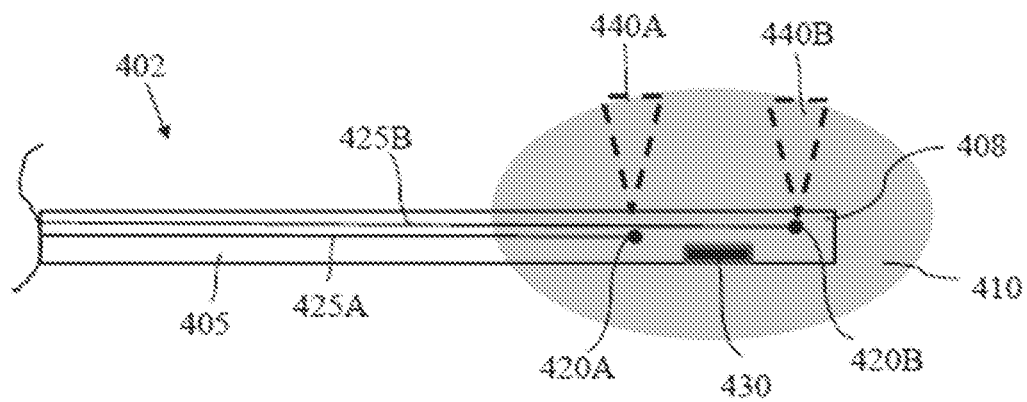
FIG. 6 is a side view of another example ablation probe that may be used on one or more ablation systems of the present disclosure.

The ablation systems of the present disclosure may include one or more probes, including those described above. Examples of the probes that may be used and are contemplated for use in the ablation systems of the present disclosure are shown in FIGS. 4-6. Referring to FIG. 4, a first example probe 400 is shown. The probe 400 may include an imaging sensor 420 and a radiofrequency (RF) emitter 430. The RF emitter 430 may be configured as a radiofrequency electrode, microwave (MW) antenna, or the like. The probe 400 may include a tubular shaft 405. The tubular shaft may define an internal bore and may be cylindrical in shape. The tubular shaft 405 may extend along an axial direction and terminate at a distal end 408. While not shown, the distal end 408 may be pointed in some examples. During an ablation treatment or other therapy, the probe 400 may be inserted into a body of a patient at a target tissue. The RF emitter 430 may be energized to produce an ablation volume 410. The imaging sensor 420 can also be operated to produce an imaging field 440 that can collect imaging data of the ablation volume 410 and target tissue.

The imaging sensor 420 can be located in the shaft 405 and be coupled to an imaging generator via connector 425. In some examples, the imaging sensor 420 can be an all-optical ultrasound transducer and the connector 425 can be an optical fiber. In other examples, other imaging sensors can be used such as electronic ultrasound sensors. The RF emitter 430 can be coupled to an RF generator via a suitable cable (not shown) that can also extend from the RF emitter through the shaft to the generator. As shown, the probe 400 can include both the imaging sensor 420 and the RF emitter 430. The imaging sensor 420 and the RF emitter 430 can be located adjacent to each other and/or spaced from one another at a predetermined distance. The position of the imaging sensor 420 relative to the RF emitter allows the imaging field 440 to be located at the ablation volume 410. In this manner, imaging data can be collected for the ablation volume without interference of surrounding tissues or other body structures and without the need for separately or independently positioning the imaging sensor relative to the RF emitter and/or the ablation volume.

In some examples, the imaging sensor 420 emits the imaging field 440 and can be rotated within the shaft 405 to allow up to a 360° view and mapping of the ablation area 410. The imaging data can be collected, for example, in cross sectional slices. The imaging sensor 420 can be coupled to the connector 425 (e.g., optical fiber) using a fiber optic rotary joint (FORJ) and/or a mechanical clip ring (SR) that may allow rotation of the imaging sensor 420. In other examples, a combination SR-FORJ arrangement can be used. While not shown, the antenna 430 can be connected via a wire to a generator that may generate microwave energy or other signals to be emitted from the antenna 430. The connector 425 may be rotated to rotate the sensor 420, in some examples. In other examples, the sensor 430 may be configured as a phased array of transducers as previously described. In such an example, the connector 425 may be stationary and not rotate since such rotation is not required to obtain 360° imaging. In other examples, multiple wires or connectors 425 may be positioned in the shaft 405 with each wire coupling a transducer of the array of transducers to an imaging generator, controller or computing device.

As described, the connector 425 and the cable connecting the imaging sensor 420 and the RF emitter 430, respectively, to their corresponding generators can be routed through the shaft 405. In other examples, one or the other or both of the connector 425 and the cable can be routed outside of the shaft 405, be embedded in the wall of the shaft 405 or be routed along the shaft 405. In still further examples, the connector 425 and/or the cable can be located along the shaft 405 in a separate conduit structure.

The probe 400 may be operated in some examples to simultaneously energize the RF emitter 430 and obtain imaging data via the imaging sensor 420. Such operation is possible because the imaging sensor 420 may be configured as an all-optical ultrasound transducer that does not suffer from interference effects between the all-optical ultrasound transducer and the RF emitter 430 (e.g., microwave antenna) because the light signals of the all-optical ultrasound transducer are not disturbed by electromagnetic noise caused by the RF emitter 430. In other examples, such as embodiments in which a piezo transducer or other transducer is used, the ablation and imaging operations may be alternated in order to prevent electromagnetic interference. For example, the ablation cycle may be performed for 1 minute and then turned off of a period of 5 seconds during which imaging can be performed using the piezo or other transducer. In other examples, other cycle times can be used.

In the example shown, the probe 400 is configured to provide imaging data from inside the ablation volume 410. In other examples, the imaging sensor 420 and the RF emitter 430 can be positioned relative to one another or other/additional imaging sensors can be positioned to obtain imaging data from areas outside of the ablation volume 410. For example, the imaging sensor 420 can be positioned further away from the distal end 408 and/or from the RF emitter 430 so that the imaging field 440 captures imaging data outside the ablation volume 410. In still other examples, the positions of the RF emitter 430 and the imaging sensor 420 can be reversed whereby the imaging sensor 420 is located closer to the distal end 408 and the RF emitter is located away from the distal end 408. Such a configuration is shown in FIG. 5. The ablation probe 401 includes the RF emitter 430 and the imaging sensor in reversed positioned from that shown in FIG. 4. In other examples, the imaging sensor 420 may be configured to obtain forward-looking imaging information. In such examples, the imaging field may extend forward of the probe 400 from the distal end 408 in a direction generally in the axial direction of the probe 400. The sensor 420 may be positioned in other configurations to obtain imaging information in other directions relative to the axis of the probe 400. Such imaging fields 440 may be aligned perpendicularly, at oblique angles, or generally aligned or parallel to the axis of the probe 400. In still other examples, other configurations can be used.

Another example probe 402 is shown in FIG. 6. In this example, the probe 402 includes more than one imaging sensor. The probe 402 may be configured similarly to the probe 400 previously described but may include more than one imaging sensor. As shown, the probe 402 may include a first imaging sensor 420A and a second imaging sensor 420B. The imaging sensors 420A and 420B can also be operated to produce corresponding imaging fields 440A and 440B that can collect imaging data of the ablation volume 410 and target tissue. Each of the imaging sensors 420A, 420B can be various suitable imaging sensors such as all-optical ultrasound transducers. Each of the imaging sensors 420A, 420B may be connected to a suitable imaging generator via a corresponding connector 425A, 425B. In the example shown, the first imaging sensor 420A is positioned away from the distal end 408 by a predetermined distance and further away from the distal end 408 than the RF emitter 430. The second imaging sensor 420B can be positioned closer to the distal end 408 than the RF emitter 430. In this arrangement, the RF emitter may be positioned between the first imaging sensor 420A and the second imaging sensor 420B. In other examples, other arrangements can be used.

In other examples (not shown), the imaging sensors may be positioned such that one imaging sensor collects imaging data from inside the ablation volume 410 and the second imaging sensor collects imaging data from outside the ablation volume. In still other examples, more than two imaging sensors can be used. In other examples, multiple imaging sensors can be located further from the distal end 408 than the RF emitter 430 so that multiple imaging sensors are located on the same axial/longitudinal side of the RF emitter. In such examples, two or more imaging sensors can be located adjacent to each other with no RF emitter in between. In still other examples, other configurations and arrays of imaging sensors may be used.

Figure 7:
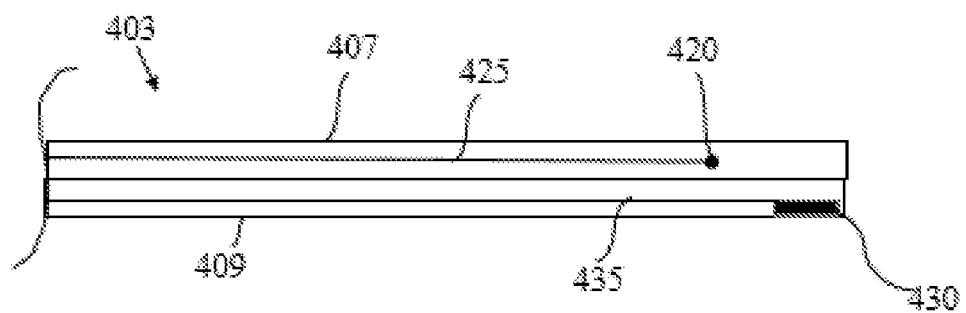
FIG. 7 is a side view of another example ablation probe that may be used on one or more ablation systems of the present disclosure.
Figure 11:
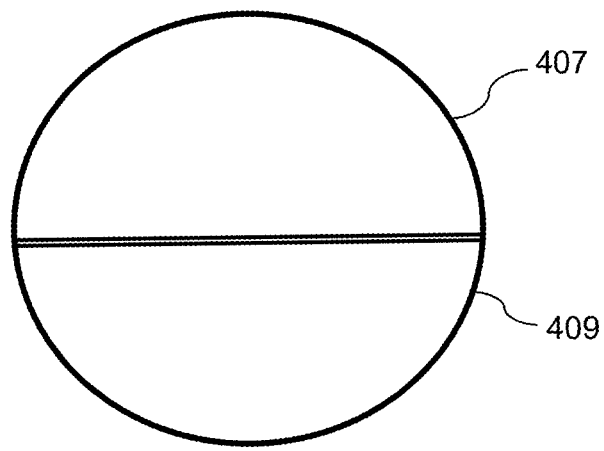
FIG. 11 is a cross section of a first shaft and a second shaft.
Figure 12:
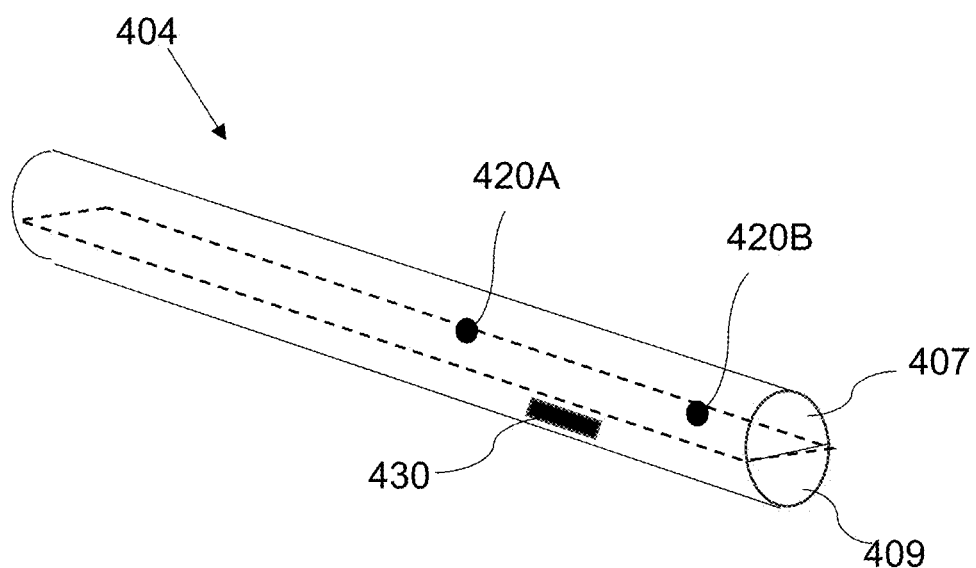
FIG. 12 is a side view of another example ablation probe that may be used on one or more ablation systems of the present disclosure.

Another example probe 403 is shown in FIG. 7. In this example, the probe 403 may include more than one shaft or conduit. In this example, the probe 403 may include a first shaft 407 and a second shaft 409. The first shaft 407 and the second shaft 409 may be configured in various structures. In some examples, each of the first shaft 407 and the second shaft 409 can be cylindrical or tubular structures. In other examples, the first shaft 407 and the second shaft 409 can have cross-sectional shapes that are semi-circles, as shown in FIG. 11. In such an example, the first shaft 407 and the second shaft 409 can be joined together to form a probe 403 that has outer profile that is circular in shape. In other examples, other shapes and structures can be used. In another example, FIG. 12 shows a probe 404 that combines features described with respect to FIGS. 6 and 7 including the RF emitter 430 positioned in the second shaft 409 and two the sensors 420A and 420B positioned in the first shaft 407.

The first shaft 407 and the second shaft 409 can be joined together using various suitable joining methods and/or attachments. In some examples, the first shaft 407 and the second shaft 409 can be joined together using an adhesive, staking, welding, or joining process. In still other examples, the probe shell can be formed as one piece to have a first shaft 407 and second shaft 409.

In the example shown, the imaging sensor 420 and the connector 425 are positioned in the first shaft 407 and the RF emitter and a cable 435 can be positioned in the second shaft 409. In this manner the imaging components and the RF components can be separated and/or insulated from one another. In other examples, the probe 403 may include more than two shafts. Such embodiments may be used, for example, in situation in which the probe 403 includes more than one imaging sensor. In such an example, each of the imaging sensors and the corresponding connector can be located in an individual shaft or conduit.

Figure 8:
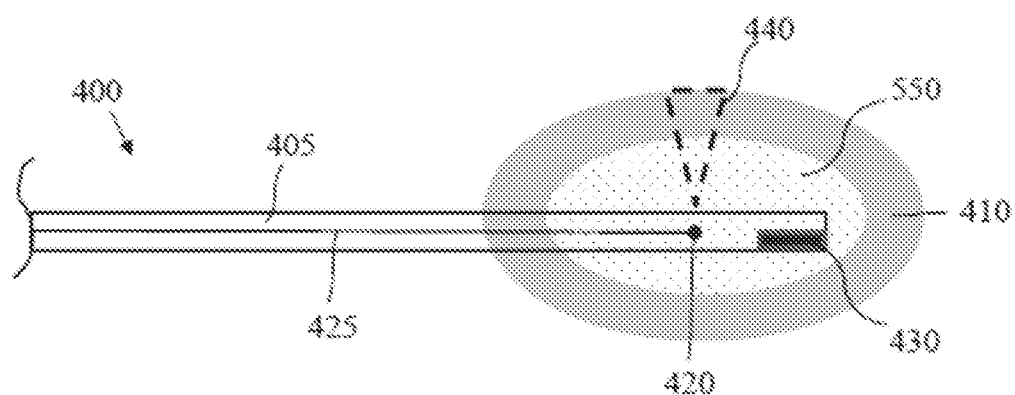
FIG. 8 is a side view of the example ablation probe of FIG. 4 used in an alternate mode of operation.

Referring now to FIG. 8, another mode of operation of the probe 400 is shown. As shown, the probes of the present disclosure can be operated in a shear wave elastography (SWE) mode. Such a mode of operation can be performed in addition to the up to 360° volume imaging mode of operation previously described. In this example mode of operation, the probe 400 can be used. The probe 400 shown may be configured as previously described. In addition, the other configurations, variations, and example probes can also be operated in a similar manner.

As shown, the probe 400 may be operated to energize the RF emitter 430 to produce an ablation volume 410. This area of elevated temperature surrounding a distal end of the probe 400 may cause destruction of a target tissue. In addition, a coagulation necrosis zone 550 may be produced. The imaging field 440 of the imaging sensor 420 can be used in a shear wave elastography (SWE) mode to collect elastography data. Such data can measure the elasticity and/or stiffness of the tissue in the imaging field. The coagulation necrosis zone 550 may have different elastography characteristics than the surrounding tissue. The imaging sensor 420 can be used to collect such information to characterize the properties of the tissue and to prepare an elastography map that can be overlaid on an image of the tissue. This can allow more information to be conveyed to a medical professional to determine the performance of an ablation treatment and to determine what, if any, action should be taken during the ablation procedure. Such information and the SWE mode of operation can be performed during the ablation treatment and/or simultaneously with the ablation of the target tissue.

Figure 9:
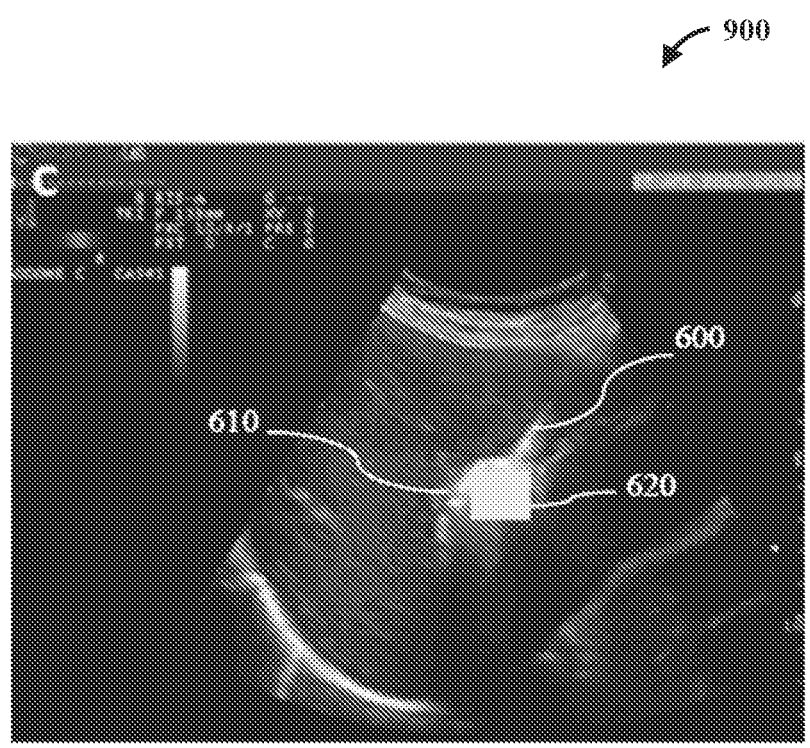
FIG. 9 is an image showing an ablation probe and a elastography map overlaid a bubble cloud that may be produced using one or more ablation systems of the present disclosure.

The probe 400, when operated in the SWE mode of operation, permits volumetric imaging of the ablation area 410 using pulse echo ultrasound and simultaneous visualization of coagulation necrosis 550 base on shear wave elastography. In such a mode of operation, the transceiver 430 can collect information about the elasticity of the surrounding tissue using acoustic radiofrequency force pulses. The information about the elasticity of the tissue in the necrosis region 550 in the ablation area 410 can be used to determine characteristics of the ablation treatment. The information collected during SWE mode of operation can, for example, be used to create an elastography map 620, as shown in FIG. 9. As shown in the image 900 (FIG. 9), the elastography map 620 can be overlaid on an ultrasound (or other) image. The elastography map 620 can provide information regarding a size, location, and elasticity of tissues in the ablation area. This information can be used in conjunction with other imaging and information to provide feedback regarding the ablation treatment. The combination of the elastography data collected by the probe 400 can be used to produce image 800 that shows a location of a probe 600, the bubble cloud 610, and the elastography map 620.

In other ablation systems and methods of the present disclosure, more one probe can be used in an ablation procedure. In such configurations, any of the various probes previously described can be used and each of the probes may have the same configuration or may be different from one another. The operation of the more than one probes can be multiplexed. For example, if multiplexed, operation of the RF emitters in multiple probes can be individually pulsed.

The probes of the present disclosure, including the examples previously described, can be single use and/or disposable. In other examples, the probes may be reusable. The probes may also be user configurable to arrange the type, location, and relative position of the RF/MW antenna/electrode, the imaging sensor(s), and/or the markers to the shaft. The ability to flexibly configure a the probes provides the user an ability to adapt the probe(s) to the particular patient and ablation situation.

Figure 10:
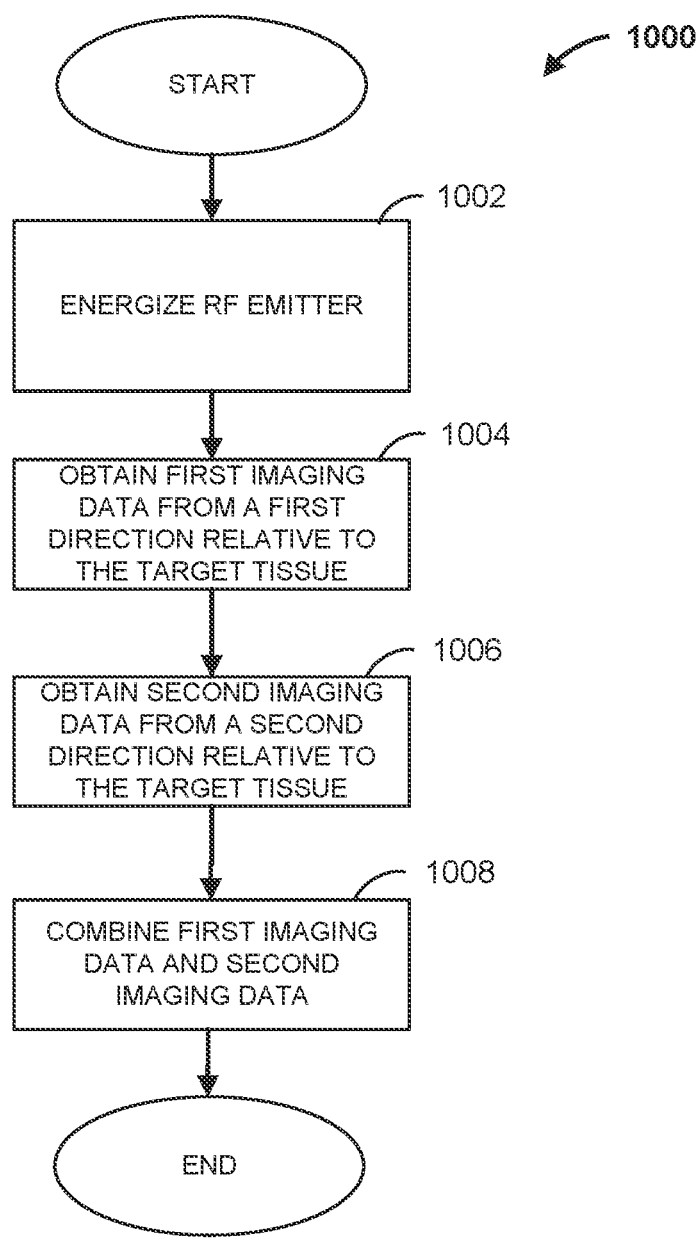
FIG. 10 is a flowchart of an example method of performing an ablation treatment in accordance with the present disclosure.

Referring now to FIG. 10, an example method 1000 of performing an ablation or RF therapy is shown. The example method 1000 may be performed using one of the ablation systems previously described that may incorporate one or more of the probes detailed above. While one or more example ablation systems and/or probes are used to describe the method 1000 below, it should be appreciated that the method 1000 is not limited to specific examples detailed below and that other alternate embodiments and examples of the ablation systems and probes of present disclosure can also be used.

The method 1000 may begin at step 1002 at which an RF emitter is energized. While not shown, prior to the performance of step 1002, a probe of an ablation system may be positioned at or near a target tissue that requires RF treatment. The distal end of the probe may be inserted into a patient and into the target tissue, for example. The RF emitter may be located inside or integrated into a probe such as that described with respect to example probes 20, 22, 24, 400, 401, 402. The RF emitter, such as an RF electrode or MW antenna, may be energized by supplying power from an RF generator to the RF emitter. This may be caused automatically by a computer, controller, or other processing device or may be initiated by a medical professional operating the ablation system. Upon energizing the RF emitter, the RF energy may generate an ablation volume at or around the target tissue as previously described.

At step 1004, first imaging data may be obtained. The first imaging data can be obtained from a first direction relative to the target tissue. The first imaging data may be obtained from a first imaging sensor. The first imaging sensor may be located on a probe and may obtain imaging data from a position inside the patient and/or from inside the ablation volume. In other examples, the first imaging data may be obtained from a location external to the patient such as by an external ultrasound transducer or from a stereotactic imaging device. The first imaging data may provide imaging information for one side or from one perspective of the target tissue.

At step 1006, second imaging data may be obtained. The second imaging data can be obtained from a second direction relative to the target tissue. The second direction may be different from the first direction of step 1004. The imaging data from the second direction may provide imaging information for a side of the ablation volume different from the first direction. The second imaging data can provide a more complete and/or a more full view of the ablation volume and the target tissue. The second imaging data can be obtained from any suitable imaging sensor as previously described. In some examples, the second imaging data may be obtained from an imaging sensor positioned on the probe that also includes the RF emitter that is energized at step 1002. In other examples, the first imaging sensor that provides the first imaging data at step 1004 and the second imaging sensor that provides the second imaging data at step 1006 are both positioned on the probe that includes the RF emitter that is energized at step 1002. In still other examples, the first imaging data and the second imaging data are obtained from imaging sensors located on different components of the ablation system.

At step 1008, the first imaging data and the second imaging data are combined. Since the first imaging data and the second imaging data are obtained from a first direction and a second direction, respectively, a more complete image of the target tissue and/or the ablation volume may be obtained than is possible using traditional imaging or ablation methods. The first imaging data and the second imaging data may be performed by an imaging engine that can operate to receive the first imaging data and the second imaging data. The imaging engine may be a component of a suitable workstation, server, computer or other processing device. While not shown, the imaging engine may further display the combined image of the target tissue and/or the ablation volume to a medical professional. The combined image may produce up to a 360° image of the target tissue and/or the ablation volume in real-time to the medical professional.

The method 1000 may be performed at least in part with a probe that includes an all-optical ultrasound transducer as the imaging sensor. In such examples, the steps of 1002 and at least one of step 1004 and/or step 1006 can be performed simultaneously. The all-optical ultrasound transducer may obtain imaging data concurrently while the RF emitter is energized.

It should be understood that the foregoing description is only illustrative of the present invention. Various alternatives and modifications can be devised by those skilled in the art without departing from the present invention. Accordingly, the present invention is intended to embrace all such alternatives, modifications, and variances that fall within the scope of the appended claims.

What is claimed is:

1. An ablation device comprising:
a shaft including a first shaft and a second shaft, wherein the first shaft and the second shaft each have a semicircular cross-sectional shape in a plane perpendicular to the longitudinal axis of the shaft;
a radiofrequency (RF) emitter positioned in the first shaft that delivers radiofrequency (RF) energy to create an ablation volume; and
a first imaging sensor and a second imaging sensor including an ultrasound transducer positioned in the second shaft and configured to obtain imaging data of the ablation volume;
wherein the RF emitter is positioned between the first imaging sensor and the second imaging sensor.

2. The ablation device of claim 1, wherein:
the shaft comprises a distal end;
the distal end is positioned at or near a target tissue during an ablation procedure; and
the RF emitter is positioned closer to the distal end of the shaft than the second imaging sensor.

3. The ablation device of claim 1, wherein the RF emitter comprises a microwave (MW) antenna.

4. The ablation device of claim 1, wherein the RF emitter comprises a radiofrequency (RF) electrode.

5. The ablation device of claim 1, wherein at least one of the first imaging sensor and the second imaging sensor comprises an optical fiber connector.

6. The ablation device of claim 1, wherein at least one of the first imaging sensor and the second imaging sensor is rotatable within the shaft.

7. The ablation device of claim 1, wherein at least one of the first imaging sensor and the second imaging sensor is configured to operate simultaneously with the RF emitter during an ablation procedure.

8. The ablation device of claim 1, wherein at least one of the first imaging sensor and the second imaging sensor is configured to operate in an imaging mode to collect imaging data and in a shear wave elastography (SWE) mode to collect elastography data from the ablation volume.

9. An ablation system comprising:
a probe configured to deliver radio frequency (RF) energy to a target tissue in a patient; wherein the probe has a shaft including a first shaft and a second shaft, wherein the first shaft and the second shaft each have a semicircular cross-sectional shape in a plane perpendicular to the longitudinal axis of the shaft;
a first imaging sensor located to obtain first imaging data from a first position relative to the target tissue; and
a second imaging sensor including an ultrasound transducer located to obtain second imaging data from a second position relative to the target tissue; wherein the second imaging sensor is located in the probe and positioned in the first shaft or the second shaft;
wherein the first position is at an opposite side of the target tissue than the second position and the second position and the second imaging sensor is located internally to the patient.

10. The ablation system of claim 9, wherein the second imaging sensor is configured to operate simultaneously with operation of the probe.

11. The ablation system of claim 9, wherein the first imaging sensor and the second imaging sensor are both located in the probe.

12. The ablation system of claim 9, wherein the second imaging sensor comprises an optical fiber connector.

13. The ablation system of claim 12, wherein the ultrasound transducer is an all-optical ultrasound transducer.

* * * * *